United States Patent [19]

Hühmer et al.

[11] Patent Number: 4,736,617
[45] Date of Patent: Apr. 12, 1988

[54] GAS SENSOR CONNECTOR

[75] Inventors: Siegfried Hühmer, Bad Oldesloe; Peter Mergenthaler, Ostrhauderfehn, both of Fed. Rep. of Germany

[73] Assignee: Dragerwerk AG, Fed. Rep. of Germany

[21] Appl. No.: 911,255

[22] Filed: Sep. 24, 1986

[30] Foreign Application Priority Data

Sep. 28, 1985 [DE] Fed. Rep. of Germany ....... 3534616

[51] Int. Cl.[4] ............................................. G01N 31/00
[52] U.S. Cl. ...................................................... 73/23
[58] Field of Search ....................... 73/23, 1 G; 422/83

[56] References Cited

U.S. PATENT DOCUMENTS 4,481,804  11/1984  Eberhard et al. ..................... 73/1 G

FOREIGN PATENT DOCUMENTS 265360  1/1971  U.S.S.R. ................................... 73/23

Primary Examiner—Stewart J. Levy
Assistant Examiner—Hezron E. Williams
Attorney, Agent, or Firm—McGlew and Tuttle

[57] ABSTRACT

A receptacle for the connection of gas sensors to a measurng gas chamber has a gas inlet including a feeding line connection for the measuring gas that is equipped with an operable shut-off element. A gas sensor holder is attached and held by a movable compression part that presses it in the direction toward the gas inlet as the gas sensor is attached to the measuring chamber. The feeding line for the measuring gas is connected into a measuring gas chamber and it is opened simultaneously and without additional manipulation and closed again after the removal of the gas sensor from the receptacle. To this end, the compression part is provided with an activating part for the shut-off element of the feeding line.

4 Claims, 2 Drawing Sheets

GAS SENSOR CONNECTOR

BACKGROUND OF THE INVENTION

Field of the Invention

This invention relates in general to devices for sensing or detecting gases and in particular to a new and useful receptacle for the automatic connection of a gas sensor to a gas source.

The invention concerns a receptacle for the connecting of gas sensors to a measuring gas chamber provided with a gas inlet, into which extends a feeding line for the measured gas equipped with an operable shut-off element and at which gas inlet a sensor holder is attached, upon which a movable compression part touches that acts in the direction toward the gas inlet. A receptacle of this type is described in the EP-A 74 498.

The known receptacle has a measuring gas chamber with a gas inlet on which the gas sensor rests centrically with its gas-sensitive measuring surface. A holding clip is clamped as compression part on the back of the gas sensor, so that the gas-sensitive measuring surface rests on the opening of the measuring gas chamber. The measuring gas, which is fed into the measuring gas chamber for the purpose of calibration in the known case, is introduced into the measuring gas chamber from separate storage containers through feeding lines, after the feeding line from the gas source to the measuring gas chamber was opened by a separate switch.

In the case of the known instrument, care must be taken that the gas-sensitive measuring surface of the gas sensor is placed accurately on the gas inlet of the measuring gas chamber and a corresponding tension lever must be attached as compression part to the back of the gas sensor, to fix the gas sensor. In addition, the gas feeding line for the measuring gas must be opened with a separate manipulation. After the completion of the measurement, or the calibration, the gas sensor can be removed from the measuring gas chamber, but the additional task of shutting off the gas feeding line again must be remembered. When this shutting off is neglected, measuring gas continues to escape from the gas feeding line through the measuring gas to flow out uncontrolled, possible unnoticeable to the user.

SUMMARY OF THE INVENTION

It is the task of the present invention to improve a receptacle for the connection of gas sensors to a measuring gas chamber in such a manner that, with the attaching of the gas sensor to the measuring gas chamber, the feeding line for the measuring gas into the measuring gas chamber is opened simultaneously and without any additional manipulation and, after the removal of the gas sensor from the receptacle, is closed again.

The solution to the stated task consists of constructing the compression part as an operating part for the shut-off element of the feeding line.

The advantage of the invention is seen mainly in the fact that now the feeding line is open and feeds the measuring gas chamber only as long as the gas sensor is held in the receptacle. An involuntary escape of the measuring gas from the measuring chamber into the environment is no longer possible when the gas sensor is detached.

The especially advantageous construction of the sensor holder as a mounting part allows the easy centering of the gas-sensitive measuring surface of the gas sensor over the gas inlet of the measuring gas chamber. The compression part is extended toward the mounting part in the form of a clamping lever in this case.

Particularly advantageous is the construction of the clamping lever with two arms and the equipping of one lever arm with a forked extension, which can receive the housing of the gas sensor. The other lever arm can be constructed as an activating part, through which a coupling of the insertion of the gas sensor into the holding device and the activation of the shut-off element can be achieved.

Particularly simple is the choice of a shut-off element in the form of a valve that can be activated through a push rod, at which the activating part of the two-armed clamping lever engages. When the forked extension of the clamping lever is thereby lifted to accept the gas sensor, the valve is opened simultaneously through the push rod and the measuring gas can now be fed into the measuring gas chamber through the feeding line. As a result, the part of the feeding line located downstream as well as the measuring gas chamber itself is rinsed with the measuring gas to be measured or the calibrating gas. When the clamping lever is released, the forked extension acts as a compression part and exerts a pressure on the gas sensor located in the mounting part, so that its gassensitive measuring surface lies against the gas inlet of the measuring gas chamber.

The forked extensions of the clamping lever are equipped on their inner surfaces with retaining shoulders that rest on a broader band of the gas sensor but glide past the narrower mounting part to ensure that the clamping lever closes the valve exclusively when the gas sensor is removed and not while the gas sensor is inserted in the mounting part. When the gas sensor is inserted, these shoulders keep the forked extension at such a distance from the gas inlet of the measuring gas chamber that the second lever arm of the clamping lever constructed as activating part activates the push rod sufficiently so that the valve remains open.

Accordingly, as an object of the invention, to provide a receptacle for the connection of gas sensors which comprises a mounting support which has a front face with a gas sample cavity and an opposite face with a gas supply feedline connection which connects into the cavity and has a control valve mounted on the support at a spaced location from the cavity which has a push rod actuator in an arrangement in which an actuating and holding lever pivotably mounted on the mounting support has one arm portion which engages a gas sensor to position it against the sensing gas cavity defined in the mounting support and an opposite arm portion which pushes the push rod to automatically open the valve when the sensor is connected and a disk to close the valve when the sensor is disconnected.

A further object of the invention is to provide a receptacle for the connection of gas sensors which is simple in design, rugged in construction and economical to manufacture.

The various features of novelty which characterize the invention are pointed out with particularity in the claims annexed to and forming part of this disclosure. For a better understanding of the invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 1:
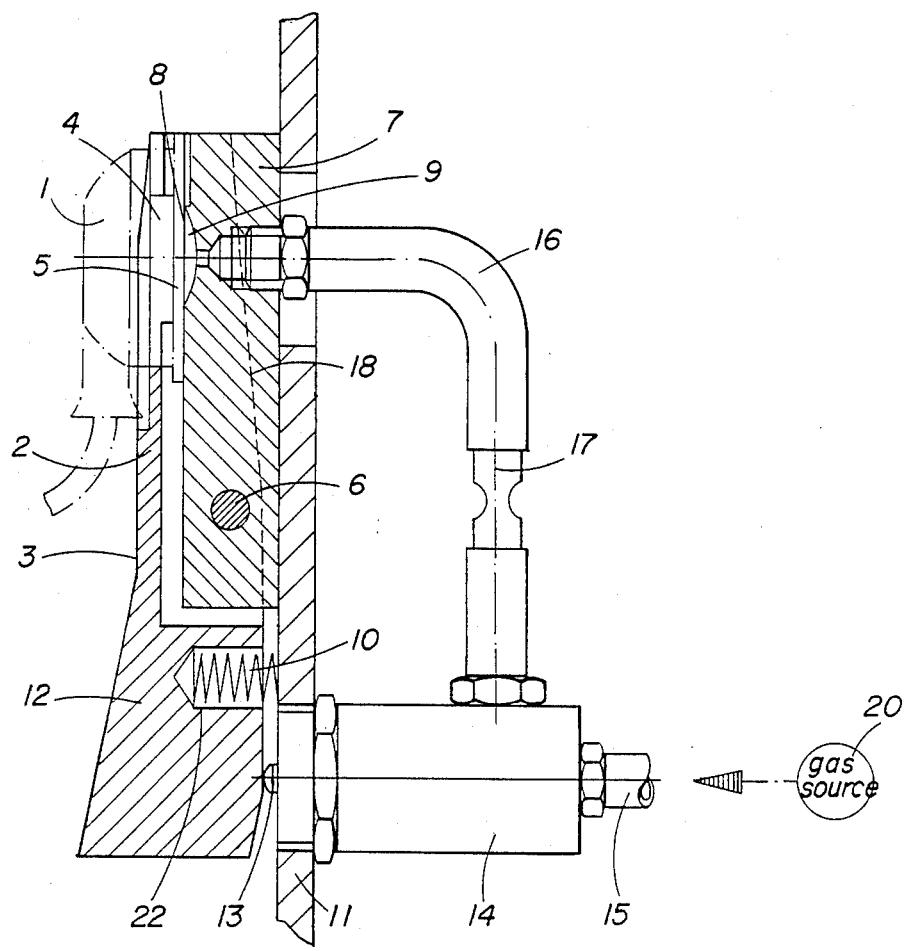
FIG. 1 is a sectional view, partially in elevation of a receptacle for the connection of gas sensors constructed in accordance with the invention.

Referring to the drawings in particular, the invention embodied therein comprises a receptacle with a connection of a gas sensor 1 to a gas sensor cavity or gas measuring chamber 9 into which gas is fed from a gas source 20 through a feed line 16. The feed line 16 which is connected to the cavity 9 has an opposite end which is connected to a valve 14 for opening and closing the feed line so as to permit gas to flow from the gas source 20 through the connecting socket 15 and the feedline 16 into the gas measuring space 9.

In accordance with the invention the receptacle includes an actuating and holding lever generally designated 12 which includes a first arm portion or a forked extension 2 which engages a sensor 1 and holds it so that it is connected to the gas cavity 9 and it has an opposite arm portion 3 which pushes a push rod actuator 13 in the direction in which the valve 14 is opened to permit the flow of gas when the senser is in place and which will close automatically on the action of a spring 10 to force the arm portion 3 away from the push rod member 13 to close the valve 14 when the sensor is removed.

In FIG. 1, gas sensor 1 is located between fork tips 19 of the forked extension 2 of compression part 3 constructed as clamping lever. The retaining shoulders 4 rest on a band 5 of sensor 1, which is thereby securely clamped into forked extension 2. Clamping lever 3, which is connected pivoted to mounting part 7 by a pivot or joint 6, presses a gas-sensitive measuring surface 8 of sensor 1 against the gas inlet of measuring gas chamber 9. The pressure required for this purpose is supplied by a compression spring 10, which acts on a point between a mounting wall 11 and activating part 12 of the clamping lever 3. The activating part 12 of the lever 3 opens a valve 14 by pressing against a depressed push rod 13, which establishes a connection between connecting line or socket 15 feeding in the measuring gas and a feeding line 16 leading into measuring gas chamber 9. A throttle 17 is located in feeding line 16.

In the shown state, the measuring gas flows from the measuring gas source 20 through the valve 14 via the feeding line 16 into measuring gas chamber 9 and can escape through its gas inlet to the gassensitive measuring surface 8 and through slight leaks that are present, into the atmosphere. When gas sensor 1 is removed from the clamping lever 3, compression spring 10 causes the upper end of side surface 18 of the compression part, shown marked by a broken line, to rest against mounting wall 11, so that the push rod 13 extends far enough through valve 14 to interrupt the feeding of measuring as through connecting socket 15.

Figure 2:
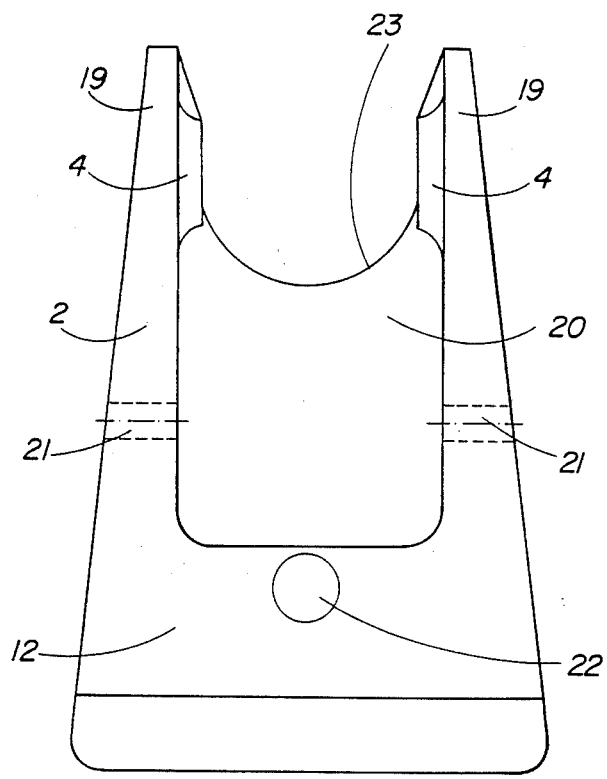
FIG. 2 is an interior elevational view of the actuating lever of the receptacle shown in FIG. 1.

The clamping lever 3 shown on its interior in FIG. 2, indicates the forked extension 2 with two fork tips 19 levering the retaining shoulders 4. The two fork tips 19 combine in the direction toward activating part 12 to form a transition piece 20, which has a covered edge 23 turned toward fork tips 19 that surrounds the gas sensor 1. Openings 21 for the insertion of the pivot or axle 6 are marked by broken lines. A bore hole 22 is provided to house compression spring 10.

While specific embodiments of the invention have been shown and described in detail to illustrate the application of the principles of the invention, it will be understood that the invention may be embodied otherwise without departing from such principles.

What is claimed is:

1. A receptacle for the connection of gas sensors, comprising a mounting support having a front face with a gas sample cavity, a gas sample line connected to said mounting support and into said feed cavity and having a control valve thereof spaced from the gas sample cavity and having a push rod actuator movably mounted in said mounting support, being movable for opening and closing said valve, an actuating and holding lever pivotably mounted on said mounting support and having a first arm portion engageable with a gas sensor to hold it against the gas sample cavity and an opposite second arm portion engageable with said push rod acutator and urging said actuator in the direction to open said feed line when a sensor is held by said first arm portion and to permit said push rod actuator to move in a direction to close said valve when said sensor is removed from said first arm portion.

2. A receptacle according to claim 1, including spring means biasing said second arm portion of said lever away from said mounting support of said first arm portion of said lever to tightly clamp the sensor.

3. A receptacle according to claim 1, including a gas source connected to said feed line through said valve, said first arm portion of said lever being bifurcated, a pivot journaled in said mounting support and pivotably supporting said actuating and holding lever.

4. A receptacle according to claim 1, wherein said actuating and holding lever first arm portion includes spaced apart legs between which the sensor is connected.

* * * * *